(12) United States Patent
Nguyen et al.

(10) Patent No.: US 10,222,365 B2
(45) Date of Patent: Mar. 5, 2019

(54) METHOD OF FORMING A LIPID BILAYER

(71) Applicant: Icahn School of Medicine at Mount Sinai, New York, NY (US)

(72) Inventors: Dac Nguyen, New York, NY (US); Basil Hanss, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/959,841

(22) Filed: Apr. 23, 2018

(65) Prior Publication Data

US 2018/0328907 A1 Nov. 15, 2018

Related U.S. Application Data

(63) Continuation of application No. 15/526,919, filed as application No. PCT/US2015/061579 on Nov. 19, 2015, now Pat. No. 9,952,195.

(Continued)

(51) Int. Cl.
*C12M 1/14* (2006.01)
*G01N 33/92* (2006.01)
(Continued)

(52) U.S. Cl.
CPC .............. *G01N 33/48* (2013.01); *C12M 1/14* (2013.01); *G01N 27/453* (2013.01);
(Continued)

(58) Field of Classification Search
CPC .............. G01N 33/48; G01N 33/483; G01N 33/48721; G01N 33/48728; G01N 33/92;
(Continued)

(56) References Cited

U.S. PATENT DOCUMENTS

2006/0251709 A1 11/2006 Ide
2009/0074988 A1 3/2009 Faris et al.
(Continued)

FOREIGN PATENT DOCUMENTS

JP 2012/081405 4/2012

*Primary Examiner* — Jennifer Wecker
(74) *Attorney, Agent, or Firm* — Leason Ellis LLP

(57) ABSTRACT

A method for forming a droplet interface bilayer (DIB) comprises the steps of: (1) providing an assembly that includes a housing contained within an enclosure, wherein the housing includes at least one aperture that comprises a cis portion and a trans portion, at least one cis electrode receptacle and at least one trans electrode receptacle, wherein the cis electrode receptacle is operatively connected to the cis portion, and the trans electrode receptacle is operatively connected to the trans portion; (2) inserting an electrode into each of the cis and trans electrode receptacles; (3) introducing an oil/lipid phase to the enclosure such that the oil/lipid phase flows into the housing through the aperture; (4) delivering at least two aqueous droplets to the oil/lipid phase in such a manner that at least one aqueous droplet is disposed within the cis portion of the aperture and at least one aqueous droplet is disposed within the trans portion of the aperture; and (5) lowering a level of the oil/lipid phase in the cis and trans portions of the aperture to cause the aqueous droplets in the cis and trans portions to expand and move closer to one another until the aqueous droplets contact one another thereby forming the lipid bilayer at the location at which the aqueous droplets contact one another.

19 Claims, 6 Drawing Sheets

Related U.S. Application Data

(60) Provisional application No. 62/082,785, filed on Nov. 21, 2014.

(51) Int. Cl.
  *G01N 33/48* (2006.01)
  *G01N 33/483* (2006.01)
  *G01N 33/487* (2006.01)
  *C12M 1/00* (2006.01)
  *G01N 27/453* (2006.01)
  *C12N 15/88* (2006.01)
  *G01N 21/77* (2006.01)
  *B01L 3/00* (2006.01)
  *G01N 33/00* (2006.01)
  *A61K 9/127* (2006.01)

(52) U.S. Cl.
  CPC ........... *G01N 33/483* (2013.01); *G01N 33/92* (2013.01); *A61K 9/127* (2013.01); *B01L 3/50273* (2013.01); *C12M 23/20* (2013.01); *C12N 15/88* (2013.01); *G01N 33/48721* (2013.01); *G01N 33/48728* (2013.01); *G01N 2033/0096* (2013.01); *G01N 2405/00* (2013.01)

(58) Field of Classification Search
  CPC ....... G01N 2033/0096; G01N 2405/00; C12M 1/14; C12M 23/20
  See application file for complete search history.

(56) References Cited

U.S. PATENT DOCUMENTS

| | | | |
|---|---|---|---|
| 2009/0167288 A1* | 7/2009 | Reid | G01N 33/48721 324/72 |
| 2010/0032627 A1* | 2/2010 | Bayley | G01N 33/5432 252/408.1 |
| 2010/0147450 A1* | 6/2010 | Takeuchi | G01N 33/68 156/245 |
| 2016/0115531 A1* | 4/2016 | Huber | C12Q 1/6869 506/4 |

* cited by examiner

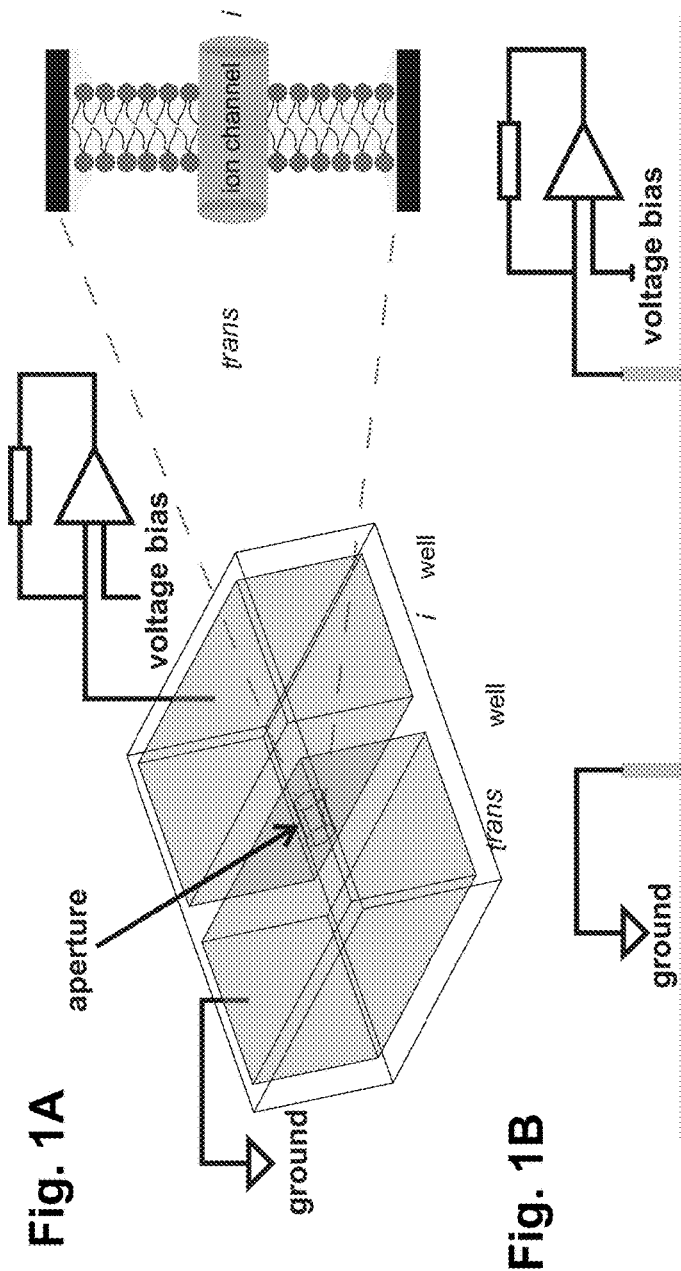
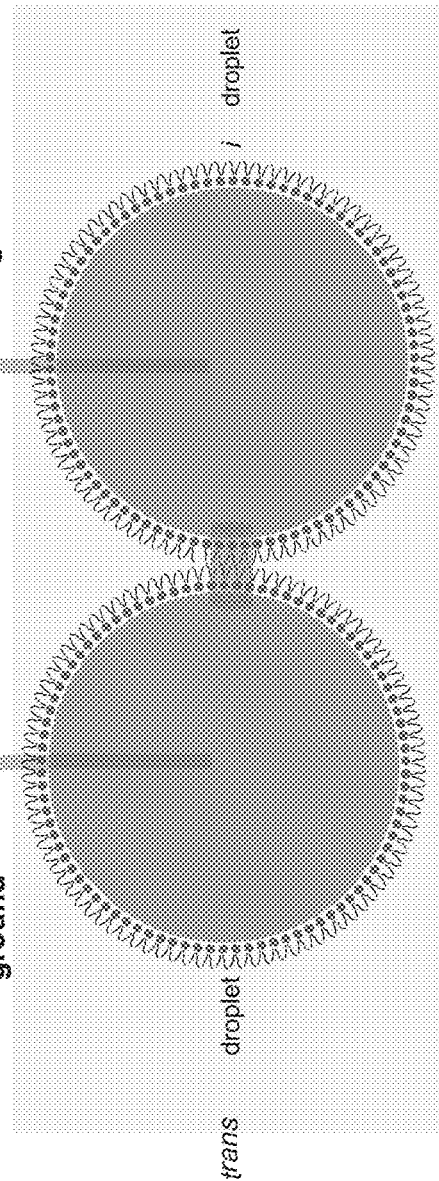
Fig. 1A
Fig. 1B

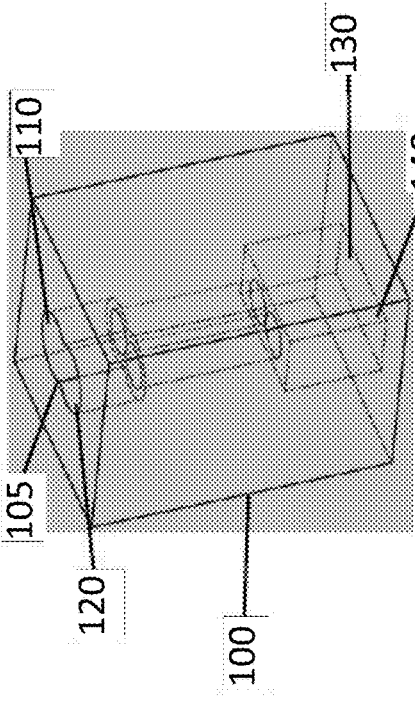
Fig. 2A
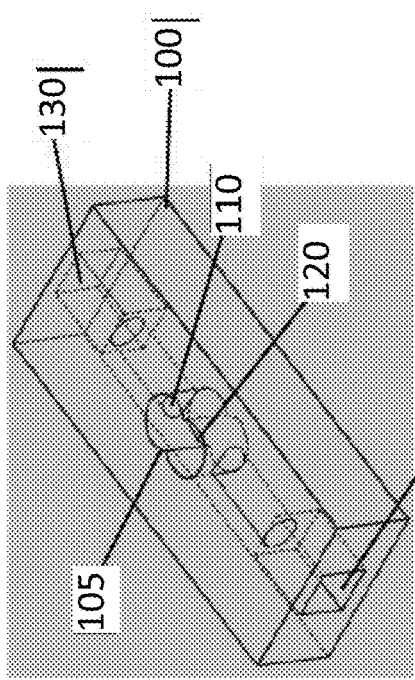
Fig. 2C
Fig. 2B
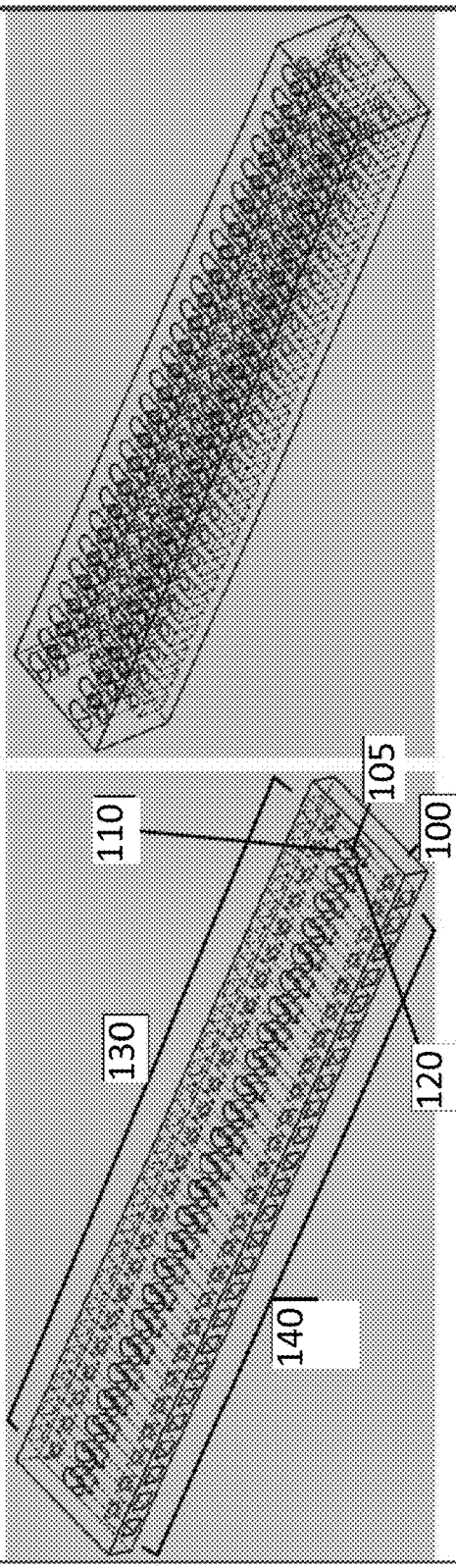
Fig. 2D

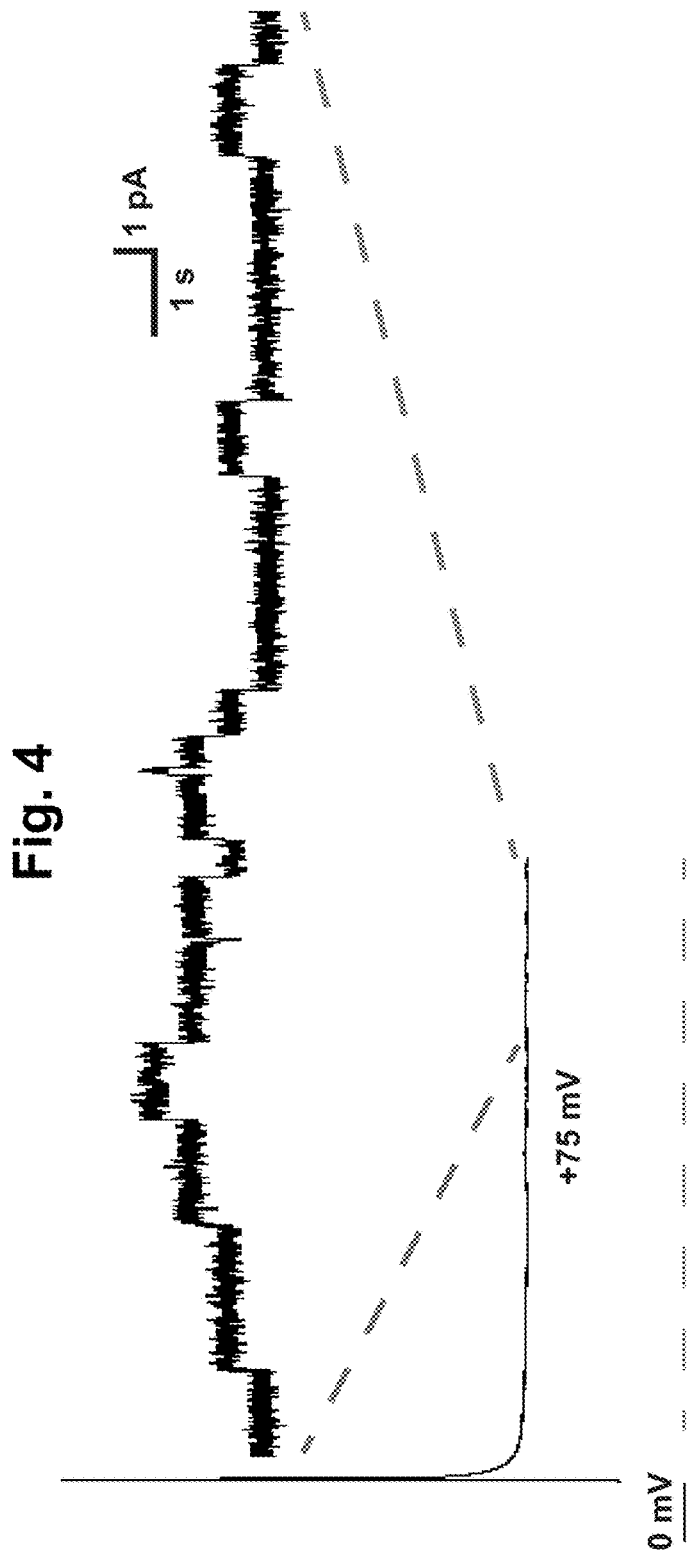

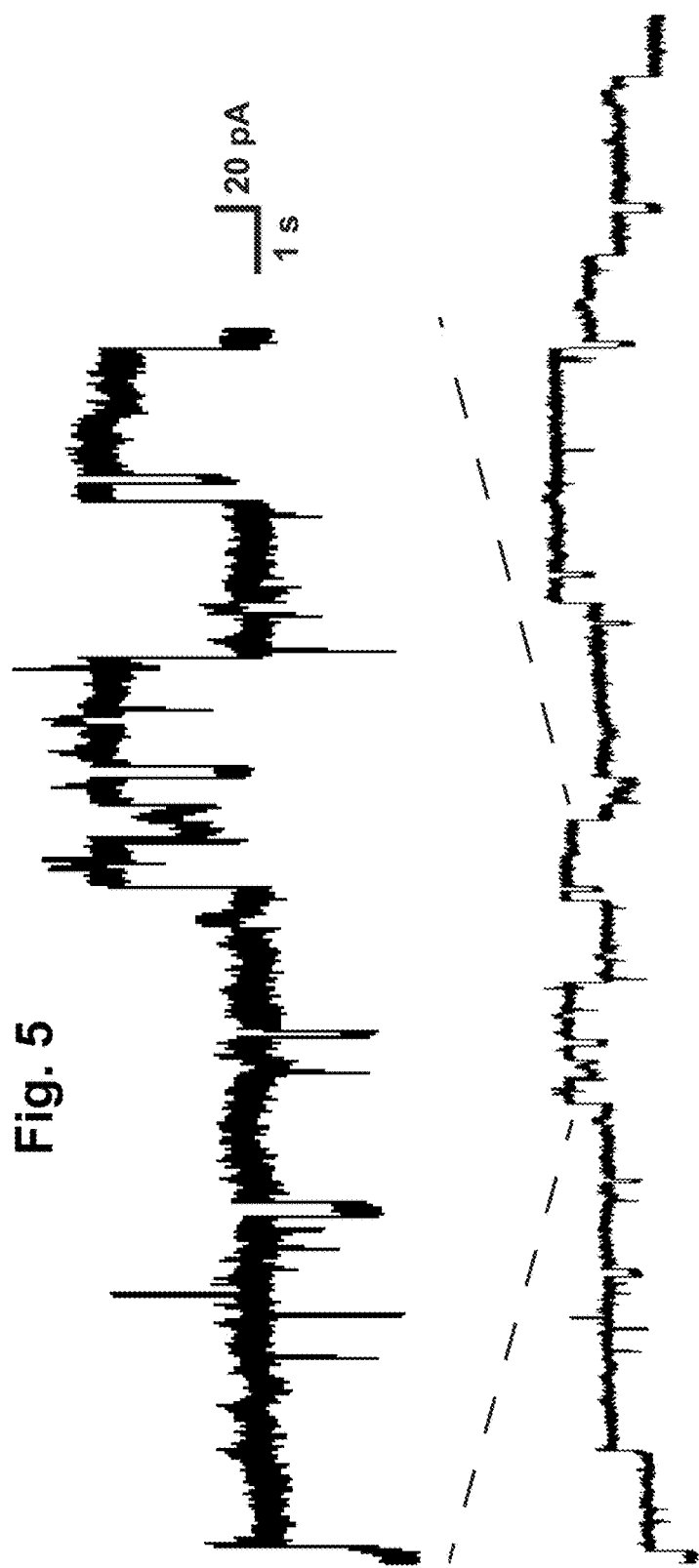

Frame 3

Frame 6

Frame 2

Frame 5

Frame 8

Frame 1

Frame 4

Frame 7

METHOD OF FORMING A LIPID BILAYER

CROSS-REFERENCE TO RELATED APPLICATIONS

This patent application is a continuation of U.S. application Ser. No. 15/526,919, filed May 15, 2017, which is a U.S. National Phase Application under 35 U.S.C. § 371 of International Patent Application No. PCT/US2015/061579, filed Nov. 19, 2015, which is based on and claims priority to U.S. Patent Application Ser. No. 62/082,785, filed Nov. 21, 2014, each of which is hereby incorporated by reference as if set forth in their respective entireties herein.

TECHNICAL FIELD

The present application relates to droplet interface bilayers, and more specifically, to a process for the formation of a droplet interface bilayer (e.g., a lipid bilayer).

BACKGROUND

An understanding of ion channels is fundamental to the study of many biophysical systems, yet several challenges hinder the ability to study ion channels. While more than 50% of all major drug targets are membrane-associated proteins, and over 400 ion channels have been identified in the human genome, only a small percentage have been cloned and functionally studied. As a result, many experimental methods have been developed for the study of ion channels. Current methods for studying ion channels consist of those that analyze ion channels at the single molecule level and those that analyze them at the ensemble level. Further, methods for studying ion channels can be separated into those that analyze ion channel behavior in synthetic settings, and those that study ion channels in biological or native-like settings.

Conventional methods using native-like or biological settings include traditional patch clamp electrophysiology systems such as those that utilize *X. laevis* oocytes as a platform for heterologous ion channel expression. Methods using the *X. laevis* oocyte are typically used to replicate and study large numbers of ion channels.

Conversely, conventional methods that use synthetic settings are typically designed for studying ion channels at the single molecule level. For example, the planar lipid bilayer technique is a method in which synthetic phospholipids are applied to a micrometer-sized opening separating two aqueous compartments, thereby forming a lipid bilayer film. The application of the phospholipids to the opening is described as "painting." After painting with the synthetic phospholipids, proteoliposomes are added to one or both aqueous compartments, and ion channel activity is then monitored using an amplifier, usually under voltage clamp conditions.

Although use of the planar lipid bilayer method for the research of ion channels has been widespread, there are several drawbacks associated with this technique and other similar methods. For example, the planar lipid bilayer method is technically demanding, and is neither robust nor scalable. Further, the lipid bilayers produced via this technique are delicate, and thus susceptible to rupture.

More recently, a droplet interface bilayer (DIB) method has been developed as an alternative to the planar lipid bilayer method. This DIB method comprises the insertion of aqueous droplets into a bulk/oil lipid phase. This DIB method, however, requires both operation in the microfluidic regime and micromanipulation. Because manipulation of nanoliter volume droplets is technically demanding and micromanipulators are bulky, expensive and preclude scalable DIB assembly, this alternative method possesses many of the drawbacks as the planar lipid bilayer method. Importantly, while improvements to the DIB assembly have been described, including droplet dielectrophoresis and digital microfluidics, these strategies require expensive, complicated and not readily accessible clean room device fabrication, iterative rapidly prototypable device design is not possible.

Although there are several contributing factors as to why so few ion channels have been studied, two predominant factors are the technical expertise needed to perform the studies and the high expense of studying ion channels in synthetic environment—drawbacks that remain a concern for conventional methods such as the planar lipid bilayer technique and the previous DIB method. Thus, there is a need for a method for producing lipid bilayers that is inexpensive, scalable, and does not require a high level of technical expertise on the part of the performer, in order to more efficiently study ion channels.

SUMMARY

The present application is directed, at least in part, to a process for forming DIBs. In one or more embodiments, a housing is produced wherein the housing includes at least one aperture that comprises a cis portion and a trans portion, at least one cis electrode receptacle and at least one trans electrode receptacle, wherein the cis electrode receptacle is operatively connected to the cis portion, and the trans electrode receptacle is operatively connected to the trans portion. In at least one embodiment, the number of cis and trans electrode receptacles equals the number of apertures. Electrodes are treated with a buffer and then inserted into each of the cis and trans electrode receptacles.

The housing including the inserted electrodes is then placed into a holder and then the holder is secured into a container, such as a petri dish. An oil/lipid phase can then be introduced into the container, wherein the oil/lipid phase enters the aperture of the housing. An aqueous droplet is then delivered into each of the cis portion and trans portion of the aperture. The droplet does not have to be applied directly to the electrode. Specifically, the droplet can re-organize spontaneously such that it becomes electrically continuous with the electrode. This re-organization can be a function of substrate adsorption and/or electrostatic substrate-lipid interaction. In other words, the aqueous droplet can be placed on the oil/lipid phase and will migrate to the electrode as a result of electrostatic attraction. It will be appreciated that this process can be manipulated by raising/lowering the oil/lipid phase or by changing the material (i.e., different charge states) that the housing is formed of. Based on the foregoing and in one embodiment, the coupling between the aqueous droplet and the electrode is thus passive in nature. A portion of the oil/lipid phase is then removed from the container, thereby removing a portion of the oil/lipid phase in the aperture. The removal of the portion of the oil/lipid phase results in the spreading of the aqueous droplets in the cis and trans portions, such that they contact one another. The DIB is then formed between the aqueous droplets at the point of contact. In one or more embodiments, the housing can support multiple apertures and corresponding electrode receptacles such that DIBs can be formed in each aperture. In at least one embodiment, the oil/lipid phase can be re-introduced into the container, thereby re-introducing it into the aperture(s) without disrupting the newly formed DIB(s), which can allow for repeated cycle of the DIB formation process. The DIBs formed in accordance with the method of the present application can be used for, inter alia, the study of ion channels as they relate to biophysical systems.

BRIEF DESCRIPTION OF THE DRAWING FIGURES

FIG. 1A shows a high-level diagram of a conventional planar lipid bilayer technique according to the prior art.

FIG. 1B shows a diagram of the formation of a lipid bilayer between two aqueous droplets located on electrode anchors of a conventional device.

FIG. 2A is perspective view of a housing in accordance with at least one embodiment of the present invention wherein the electrode receptacles are in a lateral configuration FIG. 2B is a perspective view of a housing in accordance with at least one embodiment of the present invention wherein the electrode receptacles are in a bottom configuration.

FIG. 2C is a perspective view of a housing with multiple apertures in accordance with at least one embodiment of the present invention wherein the electrode receptacles are in the lateral configuration.

FIG. 2D is a perspective view of a housing with multiple apertures in accordance with at least one embodiment of the present invention wherein the electrode receptacles are in the bottom configuration.

FIG. 4 shows an enlarged representative ~20 second current trace of single channel gramicidin A current under applied voltage bias of +100 mV following gramicidin A insertion into a millifluidic DIB assembled on a 3-D printed housing in accordance with at least one implementation of the present invention.

Figure 3A:
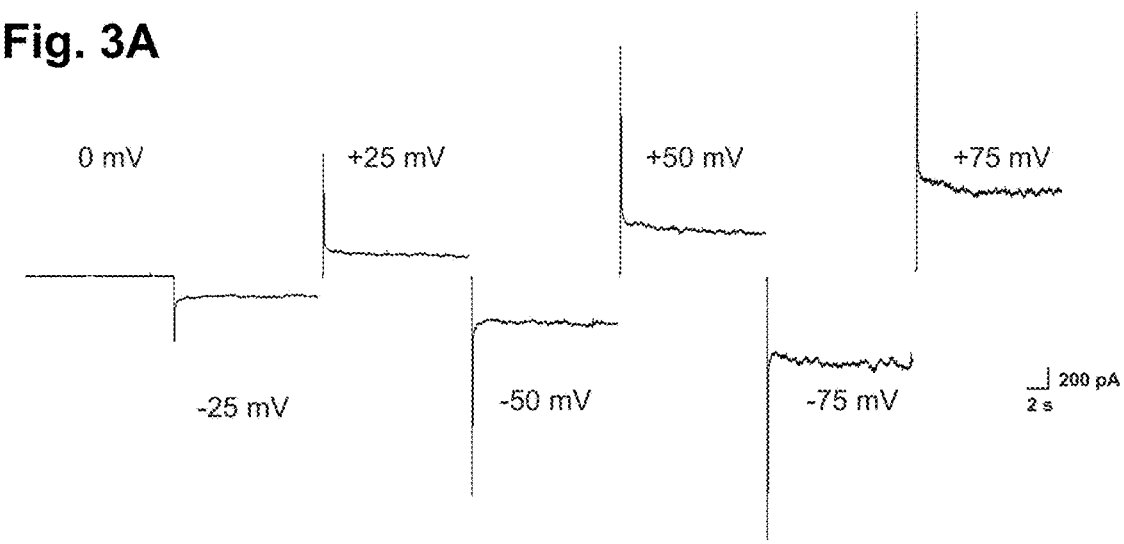
FIG. 3A shows representative current traces of ensemble gramicidin A current under varying applied voltage bias following gramicidin A insertion into a millifluidic DIB assembled on a 3-D printed housing in accordance with at least one implementation of the present invention.

FIG. 5 shows an enlarged representative ~30 second trace of single channel alpha hemolysin (aHL) current following insertion of aHL into a diphytanoylphosphatidylcholine (DPhPC) DIB (assembled on a 3-D printed housing) under an applied voltage bias of +125 mV (7 μL droplet volume, 150 mM KCl/10 mM HEPES, pH 7.18, 25 ng aHL/ml) in accordance with at least one implementation of the present invention.

FIGS. 6A-6H depict a respective series of frames 1-8 of a video taken over time showing the aqueous droplets in the oil/lipid phase in the initial separate state, then deforming as the oil/lipid level lowers, then joining to form a bilayer.

DETAILED DESCRIPTION OF CERTAIN EMBODIMENTS

Accordingly, one object of the present invention is to overcome the drawbacks of the related-art techniques described above, and provide a method for producing DIBs that is scalable, low-cost, and is not technically demanding for the performer of the process.

Traditionally, lipid bilayers were produced via methods such as the planar lipid bilayer technique (as shown in FIG. 1A), and later a DIB method. However, both methods are technically demanding and not readily scalable. In particular, the previous DIB method requires micromanipulation of the aqueous droplets to bring the droplets into contact with one another to form a lipid bilayer.

Instead of using the traditional processes to produce lipid bilayers, the present application is directed to a process for making a DIB from two aqueous drops suspended in an oil/lipid layer in a plate or the like by lowering the oil/lipid layer in the plate. FIG. 1B shows a diagram of the formation of a DIB between two aqueous droplets. As discussed herein, the process of the present application does not require micromanipulation of the aqueous droplets, and as such is not a technically demanding or expensive procedure.

FIGS. 2A-D illustrate an exemplary housing or scaffold 100 for performing the process of the present application. In one or more embodiments, the housing 100 comprises: 1) an aperture 105 for introduction of an oil/lipid phase and an aqueous phase, wherein the aperture 105 comprises a cis portion 110 and a trans portion 120; 2) a cis electrode receptacle 130; and 3) a trans electrode receptacle 140, wherein the cis and trans electrode receptacles 130, 140 are operatively (fluidly) connected to the cis and trans portions 110, 120 of the aperture 105, respectively. In at least one variation, the cis and trans electrode receptacles 130, 140 are combined into one opening.

The cis portion 110 and trans portion 120 are sections or portions of a common hole, namely, aperture 105. As shown, the portions 110, 120 can represent end sections of the aperture 105 which in the illustrated embodiment does not have a circular shape. Both portions 110, 120 provide fluid entrances into the common aperture 105.

The housing 100 can be produced in any number of ways and can be made of any type of material in accordance with the present invention so long as it is suitable for the intended applications. In at least one embodiment, the housing 100 is produced via 3-D printing and is made of acrylonitrile butadiene styrene (ABS) filament.

An electrode can be inserted into each of the cis and trans electrode receptacles 130, 140 of the housing 100. In one or more embodiments, the electrodes are AglAgCl electrodes. Prior to insertion of the electrodes, in one or more embodiments, the electrodes can be dip-coated in a buffer. In at least one embodiment, the buffer can be a 1% low-melt agarose buffer. The electrodes are secured within the electrode receptacles such that a distal end of each electrode protrudes into the cis and trans portions 110, 120 of the first aperture 105, thereby creating anchors within the cis and trans portions of the housing 100. In one or more exemplary embodiments, the electrode protruding into the cis portion of the housing 100 (cis electrode) is the voltage-holding electrode, and the electrode protruding into the trans portion of the housing 100 (trans electrode) is the ground electrode. It will be understood that the opposite arrangement is also possible in that the ground and lead electrodes can be switched and the cis electrode can be the ground electrode and the trans electrode can be voltage-holding electrode.

An advantage of the implementation is that millifluidic droplet volumes can be employed. Specifically, droplet volumes can range from the microfluidic range, as low as 200 nanoliters, to the millifluidic range, as high as 400 microliters. This provides the experimental user a dynamic range of three orders of magnitude, significantly increasing ease of experimental implementation. Additionally, with respect to tuning of electrode distance this dynamic range of droplet volumes allows the user a margin of error that makes electrode positioning for successful DIB formation trivial to satisfy. Specifically, electrodes can be positioned up to 10 mm apart in linear distance and still support successful and robust DIB formation. Conversely, if the experimental user desires smaller droplet volumes, electrodes can be positioned using a stereomicroscope as close as 200 micrometers. The advantage of an ability to use increased electrode distances is that DIB assembly can be implemented without the use of microscopy or other optical methods, thereby allowing a simpler avenue to increased throughput at lower cost. Finally, the ability to vary droplet volume of three orders of magnitude allows the user to titrate channel concentrations from the single channel level up to the ensemble channel level. Single channel levels here are taken to mean 1-4 channels present in each DIB on average. Ensemble channel levels here are taken to mean 10's to 1000's of channels present in each DIB on average.

After insertion of the electrodes into the electrode receptacles of the housing 100, the housing 100 can then be secured in a holder designed to fit within a container such as a petri dish. After the housing is secured in the holder, and the holder is placed in the container, an oil/lipid phase is introduced into the container such that the oil/lipid phase enters the aperture 105 (cis and trans portions 110, 120) of the housing 100. In accordance with one or more embodiments, the oil/lipid phase can be produced in any number of ways and can be made of any type of oil and/or lipid-based compound in accordance with the present invention so long as it is suitable for the intended applications. In at least one embodiment, the oil/lipid phase can be made from asolectin resuspended in in n-decane. In one or more embodiments, the oil/lipid phase can be made by resuspending DPhPC in n-decane.

As mentioned previously, the control characteristics of the present system can be altered by selecting/modifying the charge of the material that forms the housing (e.g., charge of a plastic housing material) and/or selecting/modifying the charge characteristics of the lipids themselves.

After the oil/lipid phase is introduced into the container, the aqueous droplets are placed onto the anchors of the electrodes located in the cis and trans portions 110, 120 of the housing 100 (the portions of the electrode protruding into the cis and trans portions [cis anchor and trans anchor]). In accordance with one or more embodiments, the aqueous droplets phase (non-continuous phase) can be produced in any number of ways and can be made of any type of compound in accordance with the present invention so long as it is suitable for the intended applications. In one or more embodiments, the aqueous droplet phase can be made from gramicidin A resuspended in KCl. In one or more embodiments, the aqueous droplet phase can be made from alpha hemolysin resuspended in a KCl/HEPES solution. In accordance with at least one embodiment, one aqueous droplet is placed on the cis anchor and one droplet is placed on the trans anchor. In one or more embodiments, the aqueous droplets can be placed on the anchors using a pipette.

After delivery of the aqueous droplets into the cis and trans portions, respectively, a portion of the oil/lipid phase is removed from the container, thereby lowering the level of oil/lipid phase in the cis and trans portions of the housing. In one or more exemplary embodiments, the portion of the oil/lipid phase is slowly removed from the container to prevent disruption of the aqueous droplets. The removal of a portion of the oil/lipid phase causes the aqueous droplets in the cis and trans portions to expand and thereby move closer to one another. The aqueous droplets eventually contact one another thereby forming a DIB (lipid bilayer) at the location at which the droplets contact one another. In one or more embodiments, the change in current (e.g., conductance) can be monitored to determine when the lipid bilayer has formed. DIB formation can be monitored either by means of a continuous capacitance measurement, macroscopic and/or microscopic optical measurement or observation of ion channel conductance above the baseline conductance of the formed DIB. In the case of macroscopic optical measurements, it is possible, for example, to employ dyes visible to the naked eye to confirm the onset of transport competence. In the case of microscopic optical measurements, it is possible, for example to employ flourophores to confirm the onset of transport competence. Optical methods confer the advantage of non-invasive DIB monitoring. As a result and accordingly, it will be appreciated that any number of different methods can be employed for monitoring the DIB formation. As mentioned above, FIG. 1B shows a diagram of the formation of a DIB between two aqueous droplets located on electrode anchors.

In one or more embodiments, following the formation of the lipid bilayer between the aqueous droplets, oil/lipid phase can be re-introduced into the container (and, as such, it is re-introduced into the cis and trans portions of the aperture) without disrupting the newly formed DIB. In one or more exemplary embodiments, the portion of the oil/lipid phase is slowly re-introduced into the container. The re-introduction of the oil/lipid phase can allow for repeated cycle of the DIB formation process and can prevent fluctuation in the bilayer interface contact area.

In one or more embodiments, the housing 100 comprises a single aperture 105 with cis and trans portions 110, 120. As discussed herein, an electrode can be inserted into the each of the cis and trans electrode receptacles 130, 140 which are operatively connected to the cis and trans portions 110, 120 of the aperture 105. In one or more embodiments, the cis electrode receptacle 130 and the trans electrode receptacle 140 are located on opposing sides of the housing 100, lateral to the aperture 105 (lateral configuration; FIG. 2A). In at least one embodiment, the cis and trans electrode receptacles 130, 140 are situated together on the bottom of the housing 100, beneath the aperture 105 (bottom configuration; FIG. 2B). A corollary of the fluidic implementation is that it becomes possible to reversibly, repeatedly and robustly bring monolayer droplets into contact to form a DIB and subsequently separate them into their original monolayer topologies. This enables the user to perform repeated statistical measures of transport activity, DIB robustness as a function of lipid composition and pharmacological activity. As a result, the present invention allows the bilayer to be "unzipped" into its original monolayer topologies.

In certain embodiments, as shown in FIGS. 2C-D, the housing 100 can support multiple apertures 105 such that DIBs can be formed in each aperture 105, and can also support multiple electrode receptacles 130, 140, wherein the number of receptacles 130, 140 equals the number of cis and trans portions 110, 120 of the apertures 105. In one or more embodiments including multiple apertures 105 and corresponding electrode receptacles, the electrode receptacles can be in a lateral configuration or a bottom configuration. FIG. 2C illustrates a housing with multiple apertures and electrode receptacles in the lateral configuration. FIG. 2D illustrates a housing with multiple apertures and electrode receptacles in the bottom configuration. In accordance with embodiments of the present application, the housing can be produced to support any number of apertures and corresponding electrode receptacles.

The process of the present application provides several advantages over the prior art. First, it removes the need for bulky, expensive micromanipulators, because the distance between the electrodes does not need to be manipulated to form the DIB. Second, it is not technically demanding, and thus removes the requirement for a skilled operator. Third, because multi-aperture housing can be fabricated such that a stereotyped assembly cycle can operate across all apertures on the housing, it allows for scalable parallelization of DIB assembly. Fourth, because the method does not rely on hanging droplets (i.e., droplets that hang from the electrode), much larger droplets can be used, enabling the development of a millifluidic platform that is more robust to droplet delivery error. For example, the droplet size can be between about 50 nL and about 700 µL; however, other sizes, including ones higher, are possible. Fifth, this fluidic assembly method can be completely compatible with repeated cycling across apertures, allowing a single housing to be used, for example, to screen a target recombinant protein library at the desired statistical depth. Consequently, a 416-aperture housing occupying a negligible bench top footprint, for example, can be used to screen the complete human ion channel proteome at a pre-determined statistical depth of, for example, 10× depth, rather than being limited to 1× depth single cycle use. Additionally, in one or more embodiments, the process of the present application is future-compatible with fluidic and robotic operations. Specifically, in at least one embodiment, the process can be practically implemented on a fluidic and/or robotic platform for proteome-scale experimentation. It will be understood that the system and process of the present invention can used/implemented in a wide range of applications and more particularly, the teachings of the present invention can be used to explore different facets of the biology including but not limited to: proteins, biological modulators, synthetic modulators (e.g., drugs), lipids (including metabolome and lipid content analyses), organic and aqueous solvents, electrical properties, other high throughput uses, etc. For each of these biological spaces, the present invention provides therapeutic discovery value and can be implemented.

FIGS. 6A-6H show a series of freeze frames (respectively labeled as frames 1-8) that were captured from a continuous real-time video of an exemplary DIB assembly in a 3D-printed side-addressed DIB scaffold in accordance with the present invention. The surrounding oil/lipid phase consists of hexadecane/lecithin (20 mg lecithin/mL hexadecane). The aqueous droplets consist of Tris-buffered distilled, de-ionized water, pH 7.5 (10 mM Tris, pH 7.5). Red food coloring has been added to easily visual the monolayer oil/lipid-aqueous interface of individual droplets. Individual 30 uL droplets (0.03 mL) are manually positioned on embedded cis and trans electrodes using a pipette. Starting with Frame 1 (t=0 seconds), frames shown here span a time interval of ~30 seconds during which oil/lipid phase is introduced into the DIB scaffold. Frame 3 illustrates contact of monolayer droplets in the right well, whereas contact has not yet occurred in the left well. Frame 4 (FIG. 6D) illustrates subsequent contact of monolayer droplets in the left well. Frames 5 to 8 (FIGS. 6E-6H) illustrate the end of this oil/lipid filling phase. At the end the filling phase, DIB assembly has occurred in both wells and the desired experimental measurement can begin.

EXAMPLES

Implementations of the process of the present application are hereinafter described in further detail by way of the following examples. However, the present invention is not limited to the following examples.

The following examples implementing the process of the present application utilized the following methods.

Methods

3D-Printing of Lipid Bilayer Scaffolds

All DIB scaffolds (housings) were designed using SolidWorks (Dassault Systemes, Waltham, Mass.) 3D CAD software before being converted into G-code using Skeinforge, an open-source conversion tool. G-code files were then loaded into pronterface, an open-source user interface for 3D-printing. The scaffolds were 3D-printed on an open-source, custom-built RepRap Mendel 3D printer using 1.75 mm acrylonitrile butadiene styrene (ABS) filament (Protoparadigm, Hermiston, Oreg.).

Bulk Lipid/Oil Phase Preparation

Lipids were prepared overnight prior to lipid bilayer assembly. For DIB assembly using asolectin (Sigma-Aldrich, St. Louis, Mo.), the bulk lipid/oil phase was prepared by resuspending asolectin in n-decane (MP Biomedicals, Santa Ana, Calif.) to a final concentration of 20 mg/ml. For DIB assembly using DPhPC (1,2-diphythanoyl-sn-glycero-3-phosphocholine, Avanti Polar Lipids, Alabaster, Ala.), the bulk lipid/oil phase was prepared by resuspending DPhPC in n-decane to a final concentration of 10 mg/ml. All bulk lipid/oil phase preparations were stored at 4° C. in the dark until use.

Non-continuous Droplet Phase Preparation

For ensemble DIB recordings, gramicidin A (gA, Sigma-Aldrich) was resuspended in 100 mM KCl at a final concentration of 100 ng/ml. For single channel DIB recordings, gA was resuspended in 100 mM KCl at final concentration of 1 ng/ml. Alpha hemolysin (aHL, Sigma-Aldrich, St. Louis, Mo.) was resuspended in 150 mM KCl/10 mM HEPES, pH 7.4. Droplet phase preparations were stored at 4° C. until use.

Lipid Bilayer Assembly on 3D-printed Scaffolds

AglAgCl electrodes were prepared by soldering either 0.1 mm or 0.5 mm diameter silver wire to one end of 0.1" pitch male/male 6" jumper wire (Mouser Electronics). The silver wire-bearing end of the jumper wire was then immersed in sodium hypochlorite (Sigma-Aldrich, St. Louis, Mo.) for 10 minutes at room temperature in the dark. Prior to use, AglAgCl electrodes were dip-coated in a 1% low-melt agarose (Fisher Scientific, Pittsburgh, Pa.) buffer made up from either 100 mM KCl (for gA recordings) or 150 mM KCl/10 mM HEPES, pH 7.4 (for aHL recordings) [20]. Once prepared, electrodes were inserted into cis and trans electrode receptacles embedded in each DIB scaffold. As noted above, electrode distance can range from 10 millimeters to 200 micrometers. Scaffolds were then secured in a 3D-printed holder designed to securely fit into a 15 mm diameter petri dish (Fisher Scientific, Pittsburgh, Pa.). After addition of the bulk oil/lipid phase to the petri dish, 7 µL aqueous droplets were manually pipetted onto both the cis and trans electrode. After ~5 minutes, the bulk oil/lipid phase was slowly manually removed to allow the aqueous droplets to "spread out" and contact each other. Following contact, the previously removed volume of bulk oil/lipid phase was slowly re-introduced.

Ensemble and Single Channel Recording

For all DIB scaffolds used, the cis droplet was positioned on the inserted voltage-holding electrode and the trans droplet was positioned on the ground electrode. Ensemble and single channel current recordings were captured and digitized at 1 kHz using an Axopatch 200B amplifier connected to a CV203BU headstage controlled by PCLAMP v10.0 (Molecular Devices, Foster City, Calif.).

Applications for the Study of Ion Channel Biophysics

The current biophysical gold standard for assessing synthetic lipid bilayer techniques entails insertion of ion channels and their subsequent electrophysiological characterization. In addition to being technologically relevant, the biological nanopores gramicidin A (gA) and alpha hemolysin (aHL) have been extensively characterized in reports employing DIBs. Accordingly, both gA and aHL were used to test the DIB assembly method in accordance with at least one embodiment of the present application.

Example 1—Gramicidin A

Figure 3B:
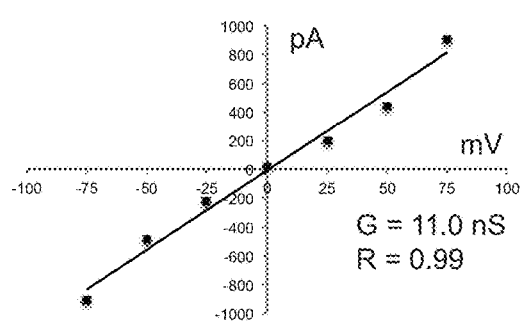
FIG. 3B shows a characteristic current-voltage curve displaying ensemble gramicidin A conductance.
Figure 3C:
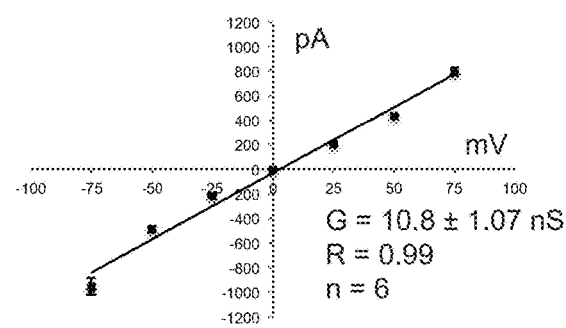
FIG. 3C shows a characteristic current-voltage curve displaying ensemble gramicidin A conductance over an average of six experiments.
Figure 6C:
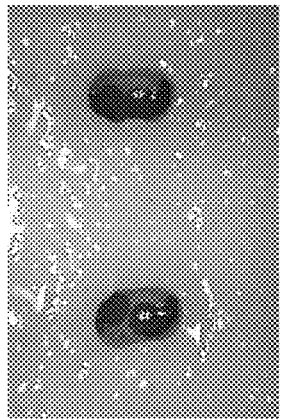
Figure 6F:
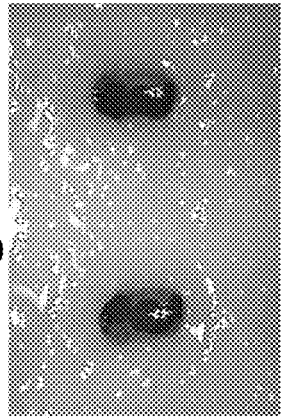
Figure 6B:
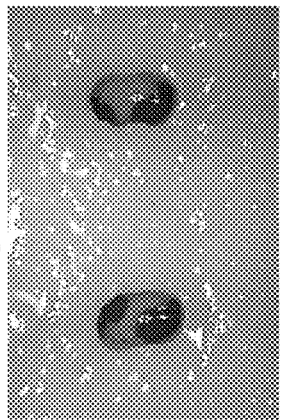
Figure 6E:
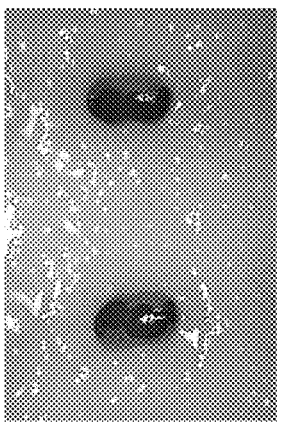
Figure 6H:
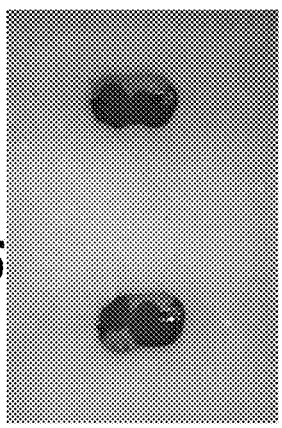
Figure 6A:
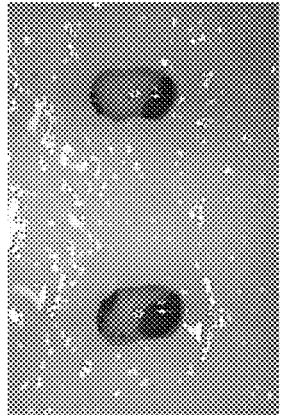
Figure 6D:
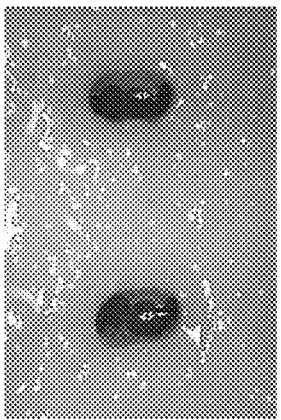
Figure 6G:
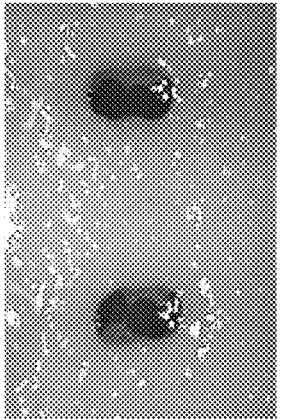

Gramicidin A (gA) is a linear pentadecapeptide antibiotic derived from *Bacillus brevis*, perhaps best known for its reported crystal structure in 1998, the first example of ion-selective pore at atomic resolution. It has subsequently become a canonical model of concentrated study in biophysics and synthetic protein engineering. Ion channels formed from gA monomers have been extensively studied and they are known to only form functional ion channels upon dimerization of gA monomers that span the thickness of a single lipid bilayer. They are, therefore, commonly used as a gold standard for assessing synthetic lipid bilayer unilamellarity. While gA is commonly titrated down to concentrations low enough to allow for observation of single channel activity in DIB, to test the robustness of the method of the present application, this experiment was used to determine whether it would be possible to support larger magnitude ensemble gA current without DIB breakdown. FIG. 3A shows representative current traces of ensemble gA current under varying applied voltage bias following gA insertion into a millifluidic DIB assembled on a 3D-printed scaffold (7 µl droplet volume, 100 mM KCl, 100 ng gA/mL). FIG. 3B shows the characteristic current-voltage curve generated from the traces shown in FIG. 3A, indicating an ensemble gA conductance of 11.0 nS. Over an average of six such experiments, a similar ensemble gA conductance of 10.8±1.07 nS was observed, illustrated in FIG. 3C.

In a subsequent experiment, the suitability of these scaffolds for single channel recording was determined by titrating gA concentrations down to values previously reported to be sufficient for discrimination of single molecule events. FIG. 4 shows a representative ~20 second current trace of single channel gA current under an applied voltage bias of +100 mV following gA insertion into a millifluidic DIB assembled on a 3D-printed scaffold (7 µl droplet volume, 100 mM KCl, 1 ng gA/ml). Analysis of the trace shown in FIG. 4 revealed a single channel gA conductance of 20.7 pS. Over an average of six such experiments, a gA conductance of 20.2±0.73 pS was observed, in good agreement with previously reported values of 18 pS and 20 pS. This titration from ensemble current magnitude down to single channel magnitude demonstrates robust operation over a dynamic range spanning over three orders of magnitude (~1 pA-~1 nA), making it suitable for both the study of both ensemble and single channel biophysics.

Example 2—Alpha Hemolysin

Alpha hemolysin (aHL), a biological nanopore, is of great interest for its potential use as a molecular sequencing machine at single nucleotide resolution. Functionalized aHL has been shown to be capable of sequencing single stranded DNA (ssDNA) down to single nucleotide resolution. To demonstrate the utility of 3D-printed DIB scaffolds in accordance with the present application for use as a tool to screen proteomes for other biological nanopores of technological interest, single channel aHL insertion was characterized into millifluidic DIB assembled on 3D-printed DIB scaffolds. FIG. 5 shows a representative ~30 second trace of single channel aHL current following aHL insertion into a DPhPC DIB under an applied voltage bias of +125 mV (7 µl droplet volume, 150 mM KCl/10 mM HEPES, pH 7.18, 25 ng aHL/ml). Analysis of the trace shown in FIG. 5 indicates a single channel aHL conductance of 0.53 nS. Over an average of six such experiments, a mean single channel aHL conductance of 0.50±0.03 nS was observed, in good agreement with previously reported values of ~0.44 nS, ~0.48 and ~0.67 nS. This observation demonstrates that 3D-printed DIB scaffolds can support complex multimeric biological nanopore assembly down to single molecule resolution, making it a suitable screening platform to expand the space of this class of technologically promising macromolecules.

Regarding the DIB scaffold substrates, a number of different materials/compositions can be used to form these substrates and are typically selected in view of desired robustness, biophysical and physicochemical characteristics of the DIB. For example, the use of negatively charged substrate could be used to spontaneously re-organize monolayer droplets in a positively charged lipid environment. This electrostatic interaction presumably affects both the time to DIB assembly and the geometry of the DIB itself. As a number of ion channels have been shown to be so far only capable of synthetic reconstitution under particular charge ratio conditions, the case could be made that different substrates should be employed to reconstitute particular ion channels and or ion channel families. Substrates considered include: ABS, polycarbonate and polymethylmethacrylate.

Regarding manufacturing methods, we envision both additive and subtractive methods will be employed depending on the desired application. For example, additive methods like 3D-printing can be employed when complex internal fluidic geometries are desired. Injection molding can be employed to produce scaffolds at high volume. Subtractive methods can be employed when substrate requirements preclude the use of extrusion-based methods like 3D-printing or injection molding.

While the present invention has been described above using specific embodiments and examples, there are many variations and modifications that will be apparent to those having ordinary skill in the art. As such, the described variations and embodiments are to be considered in all respects as illustrative, and not restrictive. Therefore, the scope of the invention is indicated by the appended claims, rather than by the foregoing description. All changes that come within the meaning and range of equivalency of the claims are to be embraced within their scope.

What is claimed is:

1. A process for forming a droplet interface bilayer (DIB) comprising the steps of:
   providing a housing that includes an aperture, a voltage electrode, and a ground electrode;
   filling the aperture with an oil/lipid phase;
   placing an aqueous droplet onto each of the voltage and ground electrodes; and
   forming a lipid bilayer in the aperture by removing a portion of the oil/lipid phase from the aperture whereby the aqueous droplets expand into the aperture until the lipid bilayer forms between the aqueous droplets.

2. The process of claim 1, wherein the voltage and ground electrodes are positioned 200 micrometers to 10 millimeters apart in linear distance.

3. The process of claim 1, wherein the aqueous droplet is between 200 nanoliters and 400 microliters in volume.

4. The process of claim 1, wherein the voltage and ground electrodes are AglAgCl electrodes treated with a 1% low-melt agrose buffer.

5. The process of claim 1, wherein the oil/lipid phase is azolectin suspended in n-decane or DPhPC suspended in n-decane.

6. The process of claim 1, wherein the aqueous droplet is gramicidin A suspended in KCl or alpha hemolysin suspended in KCl/HEPES.

7. The process of claim 1, wherein the voltage and ground electrodes are located on opposite sides of the aperture.

8. The process of claim 1, wherein the voltage and ground electrodes are located on the same side of the aperture.

9. The process of claim 1, wherein the housing is placed in a holder and the holder is secured in a container.

10. An assembly for forming a droplet interface bilayer (DIB) comprising:
    a housing that includes a voltage electrode, a ground electrode, an aperture;
    an oil/lipid phase that is contained within the housing;
    and an aqueous droplet placed on each of the voltage and ground electrodes;
    wherein the aperture comprises a droplet interface bilayer comprising the oil/lipid phase between the aqueous droplets.

11. The assembly of claim 10, wherein the voltage and ground electrodes are positioned 200 micrometers to 10 millimeters apart in linear distance.

12. The assembly of claim 10, wherein the aqueous droplet is between 200 nanoliters and 400 microliters in volume.

13. The assembly of claim 10, wherein the voltage and ground electrodes are AglAgCl electrodes treated with a 1% low-melt agrose buffer.

14. The assembly of claim 10, wherein the oil/lipid phase is azolectin suspended in n-decane or DPhPC suspended in n-decane.

15. The assembly of claim 10, wherein the aqueous droplet is gramicidin A suspended in KCl or alpha hemolysin suspended in KCl/HEPES.

16. The assembly of claim 10, wherein the voltage and ground electrodes are located on opposite sides of the aperture.

17. The assembly of claim 10, wherein the voltage and ground electrodes are located on the same side of the aperture.

18. The assembly of claim 10, wherein the housing is placed in a holder and the holder is secured in a container.

19. The assembly of claim 10, wherein the aperture has a non-circular shape and includes a cis portion that defines one end of the aperture and an adjacent trans portion that defines the other end of the aperture.

* * * * *